United States Patent [19]
Papenfuhs et al.

[11] Patent Number: 5,945,556
[45] Date of Patent: Aug. 31, 1999

[54] PROCESS FOR PREPARING N-CARBOXYMETHYLENE-4-CHLORO-ANTHRANILIC ACID AND ITS DIALKYL ESTERS

[75] Inventors: Theodor Papenfuhs, Frankfurt; Ralf Pfirmann, Griesheim; Stefan Krause; Doris Neumann-Grimm, both of Frankfurt, all of Germany

[73] Assignee: Clariant GmbH, Frankfurt, Germany

[21] Appl. No.: 09/029,414

[22] PCT Filed: Aug. 19, 1996

[86] PCT No.: PCT/EP69/03630

§ 371 Date: Apr. 14, 1998

§ 102(e) Date: Apr. 14, 1998

[87] PCT Pub. No.: WO97/08129

PCT Pub. Date: Mar. 6, 1997

[30] Foreign Application Priority Data

Aug. 31, 1995 [DE] Germany .............................. 19532054

[51] Int. Cl.⁶ .................................................. C07C 229/40
[52] U.S. Cl. ................................ 560/44; 560/43; 562/456
[58] Field of Search .......................... 560/43, 44; 562/456

[56] References Cited

U.S. PATENT DOCUMENTS

| 3,692,818 | 9/1972 | Boltze et al. ........................ 260/471 R |
| 5,821,385 | 10/1998 | Krause ..................................... 562/456 |

FOREIGN PATENT DOCUMENTS

| 0071935 | 2/1983 | European Pat. Off. . |
| 142507 | 6/1903 | Germany . |
| 1115252 | 5/1966 | Germany . |
| 1939112 | 2/1971 | Germany . |
| 2526092 | 12/1976 | Germany . |

OTHER PUBLICATIONS

J. Med. Chem. 1991, 34, 1283.
J. Prakt. Chem. 1929, 120, 64.
J. Heterocyc. Chem. 1987, 24, 811, J. Med. Chem. 1991, 34, 1283.
Dialkysulfate 102 Band 10 (no English translation).
2021863 Check for correct paragraph.
Derwent Patent Family Report and /or abstract.

*Primary Examiner*—Paul F. Shaver
*Assistant Examiner*—Brian J. Davis
*Attorney, Agent, or Firm*—Scott E. Hanf

[57] ABSTRACT

A process for preparing N-carboxymethylene-4-chloroanthranilic acid, and its dialkyl esters. The invention relates to a process for preparing N-carboxymethylene-4-chloroanthranilic acid and its dialkyl esters, which comprises reacting 2,4-dichlorobenzoic acid in the presence of a base, of a solvent and of a catalyst with glycine to give N-carboxymethylene-4-chloroanthranilic acid and, where appropriate, reacting the latter in the presence of a base and of a solvent with a dialkyl sulfate, dialkyl carbonate or alkyl halide to give the dialkyl ester.

19 Claims, No Drawings

PROCESS FOR PREPARING N-CARBOXYMETHYLENE-4-CHLORO-ANTHRANILIC ACID AND ITS DIALKYL ESTERS

The invention relates to a process for preparing N-carboxymethylene-4-chloroanthranilic acid, and its dialkyl esters.

These compounds are important starting materials for synthesizing aldose reductase inhibitors.

N-Carboxymethylene-4-chloroanthranilic acid can be prepared according to J. Med. Chem. 1991, 34, 1283 by reacting 4-chloroanthranilic acid with chloroacetic acid. The disadvantage in this case is the use of toxic chloroacetic acid in the substitution reaction. J. Prakt. Chem. 1929, 120, 64 describes the reaction of 4-chloroanthranilic acid with KCN and formaldehyde and subsequent reaction of the intermediate with aqueous KOH.

Methyl N-carbomethoxymethylene-4-chloroanthranilate is obtainable by esterifying N-carboxymethylene-4-chloroanthranilic acid with methanol/sulfuric acid (J. Heterocyc. Chem. 1987, 24,811, J. Med. Chem. 1991, 34, 1283) or with methanol/HCl (J. Prakt. Chem. 1929, 120, 64). An extremely high excess of sulfuric acid and very long reaction times are needed for the esterification.

EP 71 935 describes the following reaction sequences

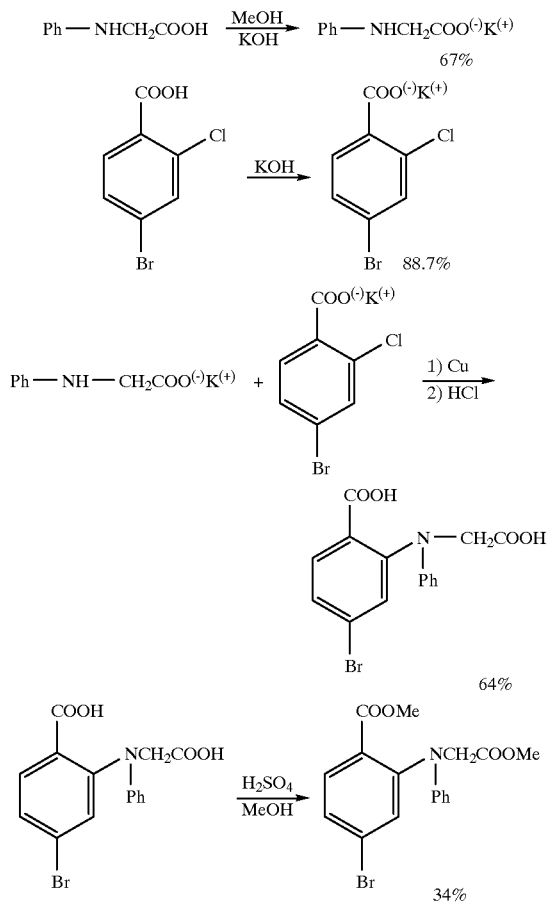

Thus the overall yield of the diester after this 4-stage synthesis (based on 3-bromo-6-chlorobenzoic acid) is only 19.3%.

There has thus been a need for a process which avoids the described disadvantages and makes N-carboxymethylene-4-chloroanthranilic acid and its dialkyl esters available in high yield and purity.

This object is achieved by a process for preparing N-carboxymethylene-4-chloroanthranilic acid and its dialkyl esters, which comprises reacting 2,4-dichlorobenzoic acid in the presence of a base, of a solvent and of a catalyst with glycine to give N-carboxymethylene-4-chloroanthranilic acid and, where appropriate, reacting the latter in the presence of a base and of a solvent with a dialkyl sulfate, dialkyl carbonate or alkyl halide to give the dialkyl ester.

It has proven suitable to prepare N-carboxymethylene-4-chloroanthranilic acid by employing 0.5 to 10 mol, advantageously 1 to 5 mol, preferably 1 to 2 mol, of glycine per mole of dichlorobenzoic acid. Solvents which can be used are dipolar aprotic solvents, for example N,N-dimethylacetamide, N,N-diethylacetamide, N,N-dimethylformamide, N-methylpyrrolidone, dimethyl sulfoxide, dimethyl sulfone, diphenyl sulfone, sulfolane, tetramethylurea, tetra-n-butylurea, 1,3-dimethyl-2-indazolidinone, water or protic organic solvents such as primary or secondary alcohols, especially high-boiling alcohols, such as ethylene glycol or glycerol, aliphatic amines or mixtures of the stated solvents. Dimethylacetamide, N-methylpyrrolidone or water have proven beneficial. Copper or copper compounds may have a catalytic effect, for example Cu or basic copper carbonate, copper iodide or mixtures thereof. 0.1 to 20 mol % of the catalyst are employed, advantageously 0.2 to 10 mol %, preferably 0.5 to 5 mol %.

It is possible to employ as base alkali metal or alkaline earth metal carbonates, bicarbonates, hydroxides, basic oxides, phosphates, hydrogen phosphates or dihydrogen phosphates, and mixtures thereof. It is advantageous to use potassium carbonate, where appropriate also in combination with an alkali metal hydroxide, preferably NaOH or KOH. The amount of base is 1 to 10 mol per mole of dichlorobenzoic acid, advantageously 1.2 to 6, preferably 1.5 to 4, mol per mole of dichlorobenzoic acid.

The reaction temperatures are kept at between 40 and 200° C., advantageously between 50 and 160° C., preferably 60 to 150° C.

The reaction times are between 30 min and 20 h, advantageously between 3 and 10 h, preferably 2 to 8 h.

The concentration of 2,4-dichlorobenzoic acid in the solvent is kept between 1 and 90% by weight, advantageously between 3 and 80% by weight, preferably between 5 and 70% by weight.

It has been found that the esterification of the two carboxyl groups can be carried out by the process according to the invention in considerably shorter times and with better yields than in the process disclosed in the literature. N-Carboxymethylene-4-chloroanthranilic acid is reacted under basic conditions with a dialkyl sulfate, dialkyl carbonate or an alkyl halide, advantageously a dialkyl sulfate, preferably with dimethyl or diethyl sulfate. 1.5 to 30 mol, advantageously 1.8 to 15 mol, preferably 2 to 8 mol, of dialkyl sulfate, dialkyl carbonate or alkyl halide are employed per mole of N-carboxymethylene-4-chloroanthranilic acid.

The solvent used is preferably water or a polar aprotic solvent such as, for example, N,N-dimethylformamide, N,N-dimethylacetamide, N,N-diethylacetamide, N-methylpyrrolidone, dimethyl sulfoxide, dimethyl sulfone, diphenyl sulfone, sulfolane, tetramethylurea, tetra-n-butylurea, 1,3-dimethyl-2-indazolidinone or mixtures thereof.

It is generally beneficial to add a base. It is possible to employ for this purpose basic organic compounds, for example amines, or basic inorganic salts, for example an alkali metal or alkaline earth metal carbonate or hydroxide, advantageously an alkali metal hydroxide or carbonate, preferably NaOH, KOH or potassium carbonate or mixtures of these components. The base is employed in amounts of 1 to 20 mol, advantageously 2 to 8 mol, preferably 2–4 mol, per mole of dicarboxylic acid.

The reaction temperatures are kept between 40 and 150° C., advantageously between 50 and 130° C, preferably between 70 and 120° C.

The reaction times are 15 min to 6 h, advantageously 30 min to 5 h, preferably 1 to 4 h.

The N-carbalkoxymethylene-4-chloroanthranilic esters can also be prepared in a one-pot reaction. In this case, yields greater than 80% (Example 5: 84%) are obtained.

When the process is carried out in 2 steps, the yields are about 85%, (Examples 2 and 3).

It was particularly surprising that the process according to the invention takes place with such good yields because another reactive group is present in the molecule in the form of the second chlorine atom, it is expressly pointed out in EP 71 935 that this leads to reaction mixtures which contain multiply substituted byproducts, which must then be removed by chromatography (page 19, lines 27 to 37).

The process steps described can be carried out under reduced, elevated or atmospheric pressure.

The following examples illustrate the invention without restricting it.

Examples of the preparation of N-carboxymethylene-4-chloroanthranilic acid:

EXAMPLE 1

47.8 g(0.25 mol) of 2,4-dichlorobenzoic acid are dissolved in 500 g of dimethylacetamide, 26.3 g (0.35 mol) of glycine and 1.7 g (7.5 mmol) of basic copper carbonate are added and the mixture is heated to 80° C. After addition of 24 g (0.6 mol) of NaOH and 22.5 g (0.16 mol) of $K_2CO_3$, the mixture is heated at 140° C. for 5 h. It is cooled to room temperature, diluted with 200 ml of water and adjusted to pH 2 with hydrochloric acid, and the crystalline product is filtered off. 43.9 g (0.19 mol, 77%) of N-carboxymethylene-4-chloroanthranilic acid are obtained.

When N-methylpyrrolidone is used in place of dimethylacetamide as solvent, essentially analogous results are obtained.

EXAMPLE 2

20 g (0.5 mol) of NaOH are dissolved in 100 ml of water, and 38.2 g (0.2 mol) of 2,4-dichlorobenzoic acid, 22.5 g (0.3 mol) of glycine and 1.4 g (6 mmol) of basic copper carbonate are added. The mixture is heated to 80° C., and 28 g (0.2 mol) of potassium carbonate are added. It is heated at 100° C. for 3 h. The filtrate after filtration with suction while hot is added to 100 ml of water and adjusted to pH 1-2 with hydrochloric acid. The product then precipitates and is filtered with suction and dried. 41 g (0.18 mol; 89%) of N-carboxymethylene-4-chloroanthranilic acid are obtained.
Examples of the preparation of alkyl N-carbalkoxymethylene-4-chloroanthranilates:

EXAMPLE 3

17 g (66 mmol) of N-carboxymethylene-4-chloroanthranilic acid are dissolved in 175 g of N,N-dimethylformamide, and 22.5 g (162 mmol) of potassium carbonate are added. At 80° C., 56 g (444 mmol) of dimethyl sulfate are added dropwise in 3 portions over the course of 2 h, and the mixture is then stirred for 30 min. The excess dimethyl sulfate is destroyed by adding ammonia. The product is precipitated by cooling, filtered off and washed with water. 16.1 g (62.5 mmol; 95%) of methyl N-carbomethoxymethylene-4-chloroanthranilate are isolated.

EXAMPLE 4

50 g (0.22 mol) of N-carboxymethylene-4-chloroanthranilic acid are dissolved in 350 ml of N,N-dimethylformamide, 60.8 g (0.44 mol) of potassium carbonate are added and the mixture is heated to 80° C. 121.8 g (0.79 mol) of diethyl sulfate are added dropwise over the course of 1.5 h and, after stirring for 45 min, a further 60.9 g (0.4 mol) of diethyl sulfate are added dropwise over the course of 75 min. The excess diethyl sulfate is destroyed by adding ammonia. The filtrate after filtration of the hot reaction mixture is added to 185 g of water, and the product is precipitated by cooling to 5° C. 32.6 g (0.114 mol; 52%) of ethyl N-carbethoxymethylene-4-chloroanthranilate are obtained.

EXAMPLE 5 (one-pot reaction)

47.8 g (0.25 mol) of 2,4-dichlorobenzoic acid, 22.5 g (0.3 mol) of glycine,1.5 g (6.8 mmol) of basic copper carbonate and 22 g (0.55 mol) of NaOH are introduced into 300 g of N,N-dimethylacetamide and heated to 80° C. 20.8 g (0.15 mol) of potassium carbonate are added, and the mixture is heated to 100° C. After 3.5 h at 100° C., the temperature is raised to 110° C., and the mixture is stirred at 110° C. for 3.5 h, during which 100 g of N,N-dimethylacetamide are added. After a further 100 g of N,N-dimethylacetamide has been added the mixture is heated at 120° C. for 2.5 h and at 140–150° C. for 2.5 h. After cooling to 80° C., 139.8 g (0.9 mol) of diethyl sulfate are added dropwise over the course of 2 h and, after stirring at 80° C. for 45 min, excess diethyl sulfate is destroyed by adding ammonia. 350 g of water are added to the reaction mixture, and the product is extracted with xylene. 352 g of xylene extract with a product content of about 0.17 g/g are obtained, corresponding to 59.8 g (84%) of ethyl N-carbethoxymethylene-4-chloroanthranilate.

We claim:

1. A process for preparing N-carboxymethylene-4-chloroanthranilic acid and its dialkyl esters, which comprises reacting 2,4-dichlorobenzoic acid in the presence of a base, of a solvent and of a catalyst with glycine to give N-carboxymethylene-4-chloroanthranilic acid and, where appropriate, reacting the latter in the presence of a base and of a solvent with a dialkyl sulfate, dialkyl carbonate or alkyl halide to give the dialkyl ester.

2. The process as claimed in claim 1, wherein 0.5 to 10 mol of glycine are employed per mole of 2,4-dichlorobenzoic acid.

3. The process as claimed in claim 1, wherein a dipolar aprotic solvent, a protic organic solvent or water is employed for the reaction of 2,4-dichlorobenzoic acid with glycine.

4. The process as claimed in claim 1, wherein the solvent employed for the reaction with glyciine is N,N-dimethylacetamide, N,N-diethylacetamide, N,N-dimethylformamide, N-methylpyrrolidone, dimethyl sulfoxide, dimethyl sulfone, diphenyl sulfone, sulfolanne, tetramethylurea, tetrra-nn-butylurea, 1,3-dimethyl-2-indazolidinone, ethylene glycol, glycerol or water.

5. The process as claimed in claim 1, wherein the concentration of 2,4-dichlorobenzoic acid in the solvent is between 1 to 90% by weight.

6. The process as claimed in claim 1, wherein the catalyst employed for the reaction of 2,4-dichlorobenzoic acid with glycine is copper carbonate or copper iodide.

7. The process as claimed in claim 1, wherein 0.1 to 20 mol % of the catalyst are employed, based on 2,4-dichlorobenzoic acid.

8. The process as claimed in claim 1, wherein alkali metal or alkaline earth metal carbonates, bicarbonates, hydroxides, oxides, phosphates, hydrogen phosphates or dihydrogen phosphates are employed as base for the reaction of 2,4-dichlorobenzoic acid with glycine.

9. The process as claimed in claim 1, wherein the amount of base for the reaction of 2,4-dichlorobenzoic acid with glycine is 1 to 10 mol based on 1 mol of 2,4-dichlorobenzoic acid.

10. The process as claimed in claim 1, wherein the reaction temperature for the reaction of 2,4-dichlorobenzoic acid with glycine is 40 to 200° C.

11. The process as claimed in claim 1, wherein the reaction times for the reaction of 2,4-dichlorobenzoic acid are between 30 min and 20 h.

12. The process as claimed in claim 1, wherein 1.5 to 30 mol of dialkyl sulfate, dialkyl carbonate or alkyl halide are employed per mole of N-carboxymethylene-4-chloroanthranilic acid for the esterification.

13. The process as claimed in claim 1, wherein the esterification is carried out with a dialkyl sulfate.

14. The process as claimed in claim 1, wherein the solvent employed for esterification is water or a polar aprotic solvent.

15. The process as claimed in claim 1, wherein amines or alkali metal or alkaline earth metal carbonates or hydroxides are employed as base for esterification.

16. The process as claimed in claim 1, wherein 1 to 20 mol of base are employed per mole of dicarboxylic acid for the esterification.

17. The process as claimed in claim 1, wherein the reaction temperature for the esterification is between 40 to 150° C.

18. The process as claimed in claim 1, wherein the reaction times for the esterification are between 15 min and 6 h.

19. The process as claimed in claim 1, wherein the reaction of 2,4-dichlorobenzoic acid with glycine and the subsequent esterification are carried out as a one-pot reaction.

* * * * *